(12) United States Patent
Christensen et al.

(10) Patent No.: US 11,959,063 B2
(45) Date of Patent: Apr. 16, 2024

(54) OPTIMIZATION OF FERMENTATION PROCESSES

(71) Applicant: UNIBIO A/S, Roskilde (DK)

(72) Inventors: Ib Christensen, Allerod (DK); Leander Petersen, Copenhagen (DK); Andre Kofoed Drejer, Copenhagen (DK); John Bagterp Jorgensen, Bunkeflostrand (SE); Sten Bay Jorgensen, Kokkedal (DK); Jorgen K. H. Knudsen, Hellerup (DK)

(73) Assignee: UNIBIO A/S, Roskilde (DK)

( * ) Notice: Subject to any disclaimer, the term of this patent is extended or adjusted under 35 U.S.C. 154(b) by 564 days.

(21) Appl. No.: 16/651,427

(22) PCT Filed: Sep. 28, 2018

(86) PCT No.: PCT/EP2018/076502
§ 371 (c)(1),
(2) Date: Mar. 27, 2020

(87) PCT Pub. No.: WO2019/063809
PCT Pub. Date: Apr. 9, 2019

(65) Prior Publication Data
US 2020/0283720 A1 Sep. 10, 2020

(30) Foreign Application Priority Data
Sep. 29, 2017 (DK) .................. PA 2017 00539

(51) Int. Cl.
*C12M 1/36* (2006.01)
*B01J 19/00* (2006.01)
(Continued)

(52) U.S. Cl.
CPC .............. *C12M 41/48* (2013.01); *B01J 19/00* (2013.01); *B01J 19/0006* (2013.01);
(Continued)

(58) Field of Classification Search
CPC ......... C12M 41/48; C12M 29/18; C12Q 3/00; B01J 19/00; B01J 19/0006; B01J 19/1837
See application file for complete search history.

(56) References Cited

U.S. PATENT DOCUMENTS

2006/0216818 A1 9/2006 Amano
2009/0117647 A1 5/2009 Buddhi et al.
(Continued)

FOREIGN PATENT DOCUMENTS

CN 102392068 A 3/2012
SU 1286627 A1 1/1987
(Continued)

OTHER PUBLICATIONS

Yamuna Rani, K., and V. S. Ramachandra Rao. "Control of fermenters—a review." Bioprocess Engineering 21.1 (1999): 77-88. (Year: 1999).*
(Continued)

*Primary Examiner* — Robert J Eom
(74) *Attorney, Agent, or Firm* — Ware, Fressola, Maguire & Barber LLP

(57) ABSTRACT

A system and a method is disclosed for adjusting and/or optimizing a fermentation process performed in one U-loop fermenter, the system including a processor and database for repetitively providing a test value of a fermenter parameter and for repetitively entering the test value of the parameter in the database; wherein the database stores multiple test value entries at various points in time and also stores multiple control value entries at various points in time, wherein the processor performs a mathematical analysis of the test value for providing a calculated test value, and/or the control value for providing at least one calculated control value; and selects, on the basis of the calculated test value and/or on the calculated control value, an adjustment to be
(Continued)

introduced into at least one other U-loop fermenter to benefit from the change made in the one U-loop fermenter.

11 Claims, 4 Drawing Sheets

(51) Int. Cl.
    *B01J 19/18*     (2006.01)
    *C12M 1/00*     (2006.01)
    *C12Q 3/00*     (2006.01)
(52) U.S. Cl.
    CPC .......... *B01J 19/1837* (2013.01); *C12M 29/18* (2013.01); *C12Q 3/00* (2013.01)

(56) References Cited

U.S. PATENT DOCUMENTS

2011/0244543 A1* 10/2011 Larsen .................. C12M 41/40
    435/41
2016/0224721 A1     8/2016 Neymann et al.

FOREIGN PATENT DOCUMENTS

WO     00/70014 A1     11/2000
WO     2008/010005 A1     1/2008

OTHER PUBLICATIONS

Danish Search Report, Application No. PA 2017 000539, completed Mar. 27, 2018, 4 pages.

International Search Report and Written Opinion of the International Search Authority, PCT/EP2018/076502, dated Dec. 21, 2018, 16 pages.

Dres Foged Olsen et al, "Modeling and Simulation of Single Cell Protein Production," Proceedings of the 17th World Congress International Federation of Automatic Control, Seoul, Korea, Jul. 6-11, 2008, vol. the distinguishing featurs 43, No. 6, Jan. 1, 2010 (Jan. 1, 2010), pp. 502-507, XP055534151, Red Hook, NY.

Iyer MS et al: "Dynamic Reoptimization of a Fed-Batch Fermenter", Biotechnology and Bioengineering, Wiley, US, vol. 63, No. 1, Apr. 5, 1999 (Apr. 5, 1999), pp. 10-21.

Ores Foged Olsen et al, "Optimal Operating Points for SCP Production in the U-Loop Reactor," Proceedings of the 17th World Congress the International Federation of Automatic Control; Seoul, Korea; Jul. 6-11, 2008., vol. 43, No. 5, Jan. 1, 2010 (Jan. 1, 2010), pp. 499-504, XP055534141, Red Hook, NY.

L.G.S. Longhi et al: "State Estimation of an Experimental Bioreactor Using the Extended Kalman Filtering Technology", Proceedings of the 17th World Congress the International Federation of Automatic Control; Seoul, Korea; Jul. 6-11, 2008., vol. 35, No. 1, Jan. 1, 2002 (Jan. 1, 2002), pp. 379-382, XP055534155, Red Hook NY.

Guang-Yan Zhu et al, "Model predictive control of continuous yeast bioreactors using cell population balance models," Chemical Engineering Science, vol. 55, No. 24, Dec. 1, 2000 (Dec. 1, 2000), pp. 6155-6167, XP055534158, GB.

Mengzhe Wu et al: "Modelling and simulation of a U-loop Reactor for Single Cell Protein Production" In: "Computer-Aided Chemical Engineering", Jan. 1, 2016 (Jan. 1, 2016), Elsevier, NL, XP055533697, ISSN: 1570-7946, vol. 38, pp. 1287-1292.

Notification of Transmittal of the International Preliminary Report on Patentability (IPRP) under PCT Rule 71.1, PCT/EP2018/076502, dated Sep. 4, 2019 (1 page), including IPRP (7 pages), and letter of Jul. 4, 2019 from applicant with amendment and arguments (6 pages), and trilingual notice (1 page), 15 pages total.

English translation of Zhi Ying Peng, "Biological denitrification of food industry wastewater using nitrifying and denitrifying bacteria", Beijing: China Light Industry Press, Aug. 31, 1999, in "Food Biotechnology", China Press, Jan. 1, 2000, pp. 324-325.

* cited by examiner

OPTIMIZATION OF FERMENTATION PROCESSES

TECHNICAL FIELD OF THE INVENTION

The present invention relates to a method for optimizing a fermentation process. In particular the present invention relates to a dynamic method for optimizing a fermentation process improving the productivity.

BACKGROUND OF THE INVENTION

Fermentation is a metabolic process that is used for providing various fermentation products from growth of microorganisms that consumes a substrate. The fermentation products may be microbial biomass, proteins, organic acids, amino acids, alcohol or other chemical compounds.

The fermentation process is a very complex process that involves a large number of variables that may influence the resulting outcome of the fermentation process and some of these variables may be independent and others may be interrelated, where the change of one variable affect the other(s) variable(s). Thus, a fermentation process comprises a large number of complex interactions of a number of variables and reactions that may be (individually or jointly) adjusted to optimize the fermentation product(s) of interest.

One such complex fermentation process is fermentation in an U-loop fermenter, an in particular the single cell protein fermentation in an U-loop fermenter, e.g. by fermenting the methanotrophic bacteria, *Methylococcus capsulatus*, where the main product is biomass material, based on methane or a methane derived substrate, such as methanol.

In such a fermentation, process control e.g. of the substrate feed, such as methane or methanol, during the start-up phase (batch process and/or feed-batch process) is of outmost importance as too little substrate feed results in a reduced biomass production and thus an impaired productivity. If substrate, e.g. methanol is over-feed the production yield will drop and in worst case the yield will drop immediately to a zero biomass production and often the fermentation process must be restarted.

Thus, to avoid failure of the traditional fermentation processes, to provide proper productivity of the fermentation process and to ensure a proper start-up, batch and feed-batch process, the substrate, e.g. methane or methanol, is under feed from optimal feeding and productivity by about 20-40% resulting in undesirable low productivity.

Hence, there are a need in the industry for an optimised fermentation process with improved productivity, in particular during the start-up phase (batch process and feed-batch process).

SUMMARY OF THE INVENTION

Thus, an object of the present invention relates to a system and a method for optimizing a fermentation process.

In particular, it is an object of the present invention to provide a system and a method that solves the above-mentioned problems of the prior art with high degree of failure and/or underfeeding of e.g. substrate to avoid significant reductions in the desired fermentation product.

Thus, one aspect of the invention relates to a system for adjusting and/or optimizing a fermentation process performed in at least one U-loop fermenter, the system comprising:
at least one U-loop fermenter being operatively connected to a computer
the computer comprising a processor and being operatively connected to a database;
at least one analysis apparatus for repetitively providing a test value of at least one parameter of one U-loop fermenter;
a data interface for repetitively entering the test value of the at least one parameter in the database,
the database comprising at least one control value,
wherein the database is adapted to store multiple database entries representing the test value of the at least one parameter at various points in time and adapted to store multiple database entries representing the control value at various points in time, wherein the processor is programmed to:
perform at least one mathematical analysis of the test value providing a calculated test value, and/or the control value providing at least one calculated control value; and
selecting, on the basis of the calculated test value and/or on the calculated control value, the adjustment to be introduced into at least one other U-loop fermenter to benefit from the change made in the one U-loop fermenter.

Another aspect of the present invention relates to a method for adjusting and/or optimize a fermentation process performed in at least one U-loop fermenter, the system comprising:
repetitively providing at least one test value of at least one parameter of one U-loop fermenter to at least one analysis apparatus;
repetitively entering the test value of the at least one parameter in a database of a computer comprising a processor;
repetitively entering at least one control value in a database of a computer comprising a processor;
wherein the database is adapted to store multiple database entries representing the test value of the at least one parameter at various points in time and adapted to store multiple database entries representing the control value at various points in time, wherein the processor is programmed to:
perform at least one mathematical analysis of the test value providing a calculated test value, and/or the control value providing at least one calculated control value; and
selecting, on the basis of the calculated test value and/or on the calculated control value, the adjustment to be introduced into at least one other U-loop fermenter to benefit from the change made in the one U-loop fermenter.

Yet another aspect of the present invention relates to the use of at least one mathematic analysis for the optimization of the performance of at least one U-loop fermenter.

BRIEF DESCRIPTION OF THE FIGURES

FIG. 2a illustrate the biomass concentration in kg/m$^3$ over time (h); FIG. 2b illustrate the substrate concentration in kg/m$^3$ over time (h); FIG. 2c illustrate the oxygen concentration in kg/m$^3$ over time (h); FIG. 2d illustrate the water flow in kg/m$^3$ over time (h); FIG. 2e illustrate the substrate flow in kg/m$^3$ over time (h); FIG. 2f illustrate the gas flow in kg/m$^3$ over time (h). The abbreviation I relates to the simulated states in the top-tank and is further described below. The abbreviation I is in the following also denoted black or black curve. The abbreviation II relates to the optimal start-up profiles and the corresponding concentrations in the top-tank when the optimal-start-up is computed using the simultaneous method and is further described below. The abbreviation II is in the following also denoted blue or blue curve. The abbreviation III relates to the optimal start-up profiles and the corresponding concentrations using a P-controller and is further described below. The abbreviation III is in the following also denoted red or red curve. The abbreviation IV relates to the optimal steady-state operating point and is further described below. The abbreviation IV is in the following also denoted green or green curve.

Figure 1A:
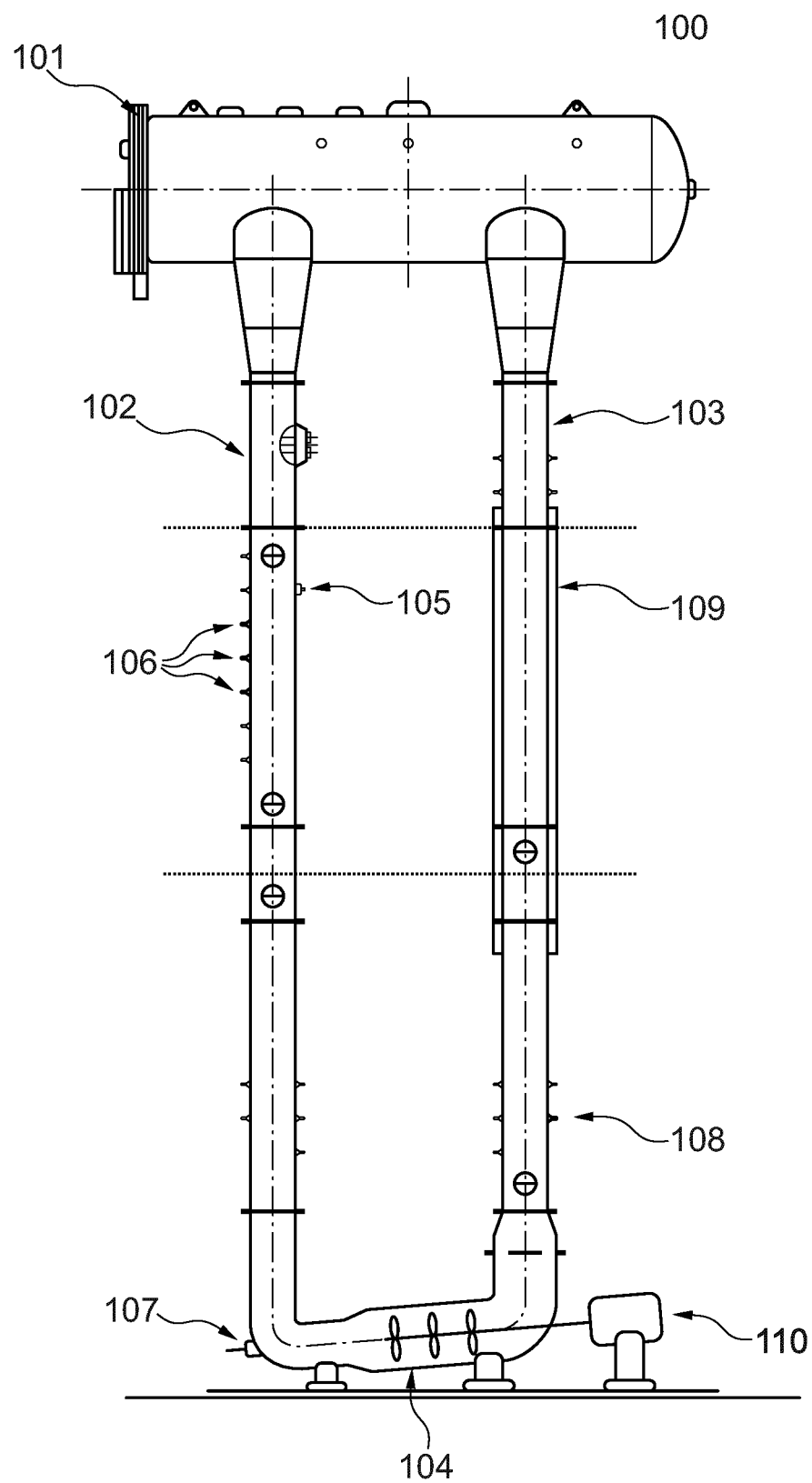
FIG. 1A shows a U-loop reactor (100), e.g. for the fermentation of the methanotroph bacteria, *Methanococcus capsulatus*; The U-loop reactor (100) comprises an essentially vertical downstream part (102), an essentially vertical upstream part (103), a U-shape bend part (104) which connects the lower ends of the downstream part (102) and upstream part (103), and a top-part (101). The U-loop reactor (100) further comprises an in-line pump (110) e.g. placed in the U-part for circulation of fermentation liquid in the reactor, a media inlet (106); a first gas inlet (105); a second gas inlet (107); a third gas inlet (108) and a heat exchanger (105).

The present invention will now be described in more detail in the following.

DETAILED DESCRIPTION OF THE INVENTION

Fermentation products, like proteins, amino acids, organic acids, and biomass which often is of a lower value than pharmaceutical compounds, are gaining greater and greater interest, however, typically the difference between the cost of producing the fermentation product, relative to the income from selling the fermentation product is often low or not even affordable. Thus, there is a huge interest in changing this relation and to make the process more productive. Accordingly, even the computation and implementation of the optimal process profiles, in particular the start-up profile, may be challenging as the optimal profile for the start-up turns out to be an unstable attractor and the start-up often ends in failure or a slow or troublesome start-up process resulting in an uneconomic production, the inventors of the present invention found a way to model the fermentation process, in particular the start-up part of the fermentation process, resulting in an optimized fermentation process with improved productivity.

When working with an U-loop fermenter (in particular during the start-up process, including the batch process and/or fed-batch process), a complex mathematical modelling is required as various sections of the U-loop fermenter may affect the fermentation process differently, during the start-up process (but also during the batch or fed-batch process). Thus, the present inventors surprisingly found a way to divide the U-loop fermenter into various elements which each may be subjected to individual mathematical modelling in order to provide a suitable mathematical modelling of the entire U-loop fermenter as a single computation would not be sufficient. In an embodiment of the present invention, the at least one mathematical analysis involves in individual mathematically modelling of at least one of the top-part, the loop-part, mixing part, the recirculating pump part, and/or the separator (or outlet). Preferably, the present invention comprises an individual mathematically modelling of the top-part, the loop-part, mixing part, and the separator (or outlet).

Hence, a preferred aspect of the present invention relates to a system for adjusting and/or optimizing a fermentation process performed in at least one U-loop fermenter, the system comprising:

at least one U-loop fermenter being operatively connected to a computer the computer comprising a processor and being operatively connected to a database;

at least one analysis apparatus for repetitively providing a test value of at least one parameter of one U-loop fermenter;

a data interface for repetitively entering the test value of the at least one parameter in the database, the database comprising at least one control value, wherein the database is adapted to store multiple database entries representing the test value of the at least one parameter at various points in time and adapted to store multiple database entries representing the control value at various points in time, wherein the processor is programmed to:

perform at least one mathematical analysis of the test value providing a calculated test value, and/or the control value providing at least one calculated control value; and selecting, on the basis of the calculated test value and/or on the calculated control value, the adjustment to be introduced into at least one other U-loop fermenter to benefit from the change made in the one U-loop fermenter.

In the context of the present invention, the term "fermentation process" relates to the process of cultivating a microorganism or a group of microorganisms by letting them reproduce in predetermined culture media under controlled conditions.

The complete fermentation process involves several stages which each involves significant different kinetics, different stoichiometric requirements, and/or different substrate demands.

Traditionally, the fermentation process may be divided into 3 main stages, the batch phase, the fed-batch phase and the continuous phase.

For commercial production, of e.g. SCP in a U-loop fermenter, the fermentation process involves 3 fermentation stages:

A batch fermentation; which is the initial propagation of the microorganisms where all materials except the microorganisms, required are decontaminated by autoclaving before, loaded to the reactor, such as the U-loop fermenter, together with the microorganisms and the process starts. The microorganism used goes through all the growth phases (lag phase, exponential phase and steady state phase). Under this operation mode, conditions are continuously changed with time under unsteady-state system and require a lot work and involvement.

A fed-batch fermentation; is a biotechnological operational process where one or more nutrients are feed to the reactor, such as the U-loop fermenter, during cultivation and in which the product/s remain in the reactor until the end of the run. The fed-batch fermentation is following the batch fermentation and is provided to achieve very high cell concentrations of the organism, as batch fermentation would require inhibitory high concentrations of nutrients and would therefore not be possible. The fed-batch fermentation is preparing the cell culture for continuous fermentation.

A continuous fermentation; is the production mode of the fermentation process where feeding the microorganism with sterile fermentation medium which is used for the cultivation of the microorganism and at the same time, removing part of the fermentation liquid comprising the cells with spent medium from the system. This makes a unique feature of continuous culture which is that a time-dependent steady-state that can be attained and which enables one to determine the relations between environmental conditions and microbial behaviour including both genetic and phenotypic expression.

For financial reasons, there is an interest and a drive in the industry to start the continuous and steady state fermentation as quickly as possible to save time and costs and provide the SCP product faster and profitable to the market.

In the context of the present invention, the start-up of the fermentation process comprises the batch phase and/or the fed-batch phase of the fermentation process. Preferably, the start-up of the fermentation process may comprise the batch phase and the fed-batch phase of the fermentation process. Even more preferably, the start-up of the fermentation process may comprise the batch phase of the fermentation process.

In a preferred embodiment of the present invention, the system may be provided for the start-up phase (the batch phase) of the fermentation process.

In another preferred embodiment of the present invention, the system may be provided for the fed-batch phase of the fermentation process.

In an even further embodiment of the present invention, the system may be provided for the continuous phase of the fermentation process.

The microorganism may be any microorganism that can be cultures in a U-loop fermenter, such as a bacterial cell, a yeast cell, a fungi cell, and/or a plant cell. Preferably, the microorganism according to the present invention is a bacterial cell.

In an embodiment, according to the present invention the fermentation process may be a single cell protein (SCP) fermentation process.

In yet an embodiment of the present invention the fermentation process may be a bacterial fermentation process. Preferably, bacteria cultivated in the fermentation process comprises a methanotrophic bacteria, preferably, the methanotrophic bacteria may be *Methylococcus capsulatus*.

The system according to the present invention may comprise one U-loop fermenter which may be adjusted and optimized based on theoretical data. The theoretical data may comprise calculated theoretical date, optionally using one or more of the models presented herein, or the theoretical data may comprise practical data obtained from one or more other U-loop fermenters, or the theoretical data may comprise a combination of calculated theoretical date, optionally using one or more of the models presented herein, and practical data obtained from one or more other U-loop fermenters.

In an embodiment of the present invention the system includes two or more U-loop fermenters being operatively connected via the computer.

The U-loop fermenter according to the present invention, may be a loop fermenter and/or an U-loop fermenter.

The inventors of the present invention surprisingly found a way to model a fermentation process performed in a U-loop fermenter, in particular the start-up part of the fermentation process, resulting in an optimized fermentation process with improved productivity. The model may include a step of dividing the fermentation into several sections which may be modelled separately by one or more models. Preferably, the models include one or more mathematical analysis.

In an embodiment of the present invention, the at least one mathematical analysis involves a correlation/relation between the test value and the control value.

In a further embodiment of the present invention the mathematical analysis involves an univariate data analysis; a multivariate data analyses; or the combination of an univariate data analysis and a multivariate data analyses.

In yet an embodiment of the present invention, the mathematical analysis involves a state estimator. In the present context, the term "state estimator" relates to the states of the model based on all the measurements. The states may preferably be the minimal information that compactly summarizes the past of the system and is needed to predict the future evolution of the system. The state estimator may preferably comprise a Kalman Filter, an Extended Kalman Filter, an Unscented Kalman Filter, an Ensemble Kalman Filter, a Particle Filter, or a Moving Horizon Estimator, or a variation of one or more of these filters.

In a further embodiment of the present invention the mathematical analysis involves a model regulator. In the context of the present invention, the term "model regulator" relates to a regulator that either drives the system to pre-defined set-points or as in economic-regulators minimizes/maximizes some objective, e.g. maximize profit or minimize operational cost, related to the process. The regulator uses the model and the estimate to predict the future evolution of the model in different scenarios and pick the best scenario (set of decisions). The model regulator may preferably involve a model predictive control, a linear model regulator and/or a non-linear model regulator.

The model regulator, the model predictive control, the linear model regulator and/or the non-linear model regulator may be based on knowledge on physical processes, on chemical and biochemical processes, data-driven models, the combination of data-driven and first-principles models.

In yet an embodiment of the present invention the model regulator may be based on a model predictive control (MPC), such as a linear MPC, an economic linear MPC, a non-linear MPC, an economic non-linear MPC.

The mathematical analysis may comprise a combination of one or more state estimator(s) and one or more model regulator(s)

In a preferred embodiment of the present invention the mathematical analysis involves a model controller. The model controller may involve a proportional (P) controller, a proportional-integral (PI) controller, a proportional-integral-derivative (PID) controller or a combination hereof.

In respect of the start-up process according to the present invention which may be considered an unstable attractor—specialized techniques for start-up of an U-loop fermenter may be required. In an embodiment of the present invention the fermentation process is a feedback based conventional strategy, PID-control technology as described herein may be used.

According to the optimization based non-linear MPC technologies, and/or in computation of the optimal trajectory, simultaneous or multiple-shooting optimization methods may be used.

The mathematical analysis preferred in the present invention may involve a state space model.

The mathematical analysis may comprise a combination of one or more state estimator(s) and one or more model controllers, or one or more model regulator(s) and one or more model controllers or one or more state estimator(s); one or more model regulator(s) and one or more model controllers.

In an embodiment of the present invention the at least one mathematic analysis involves one or more of a microbial kinetic modelling; a production modelling; a growth rate modelling; a substrate modelling; a stoichiometric modelling; a mechanical modelling (mixing rate, the size of the U-loop fermenter, the flow rate, the pressure generating devices, the temperature regulating devices); or a U-loop fermenterdesign modelling.

In a further embodiment of the present invention the at least one mathematic analysis involves one or more modelling, such as two or more modelling, e.g. three or more modelling, such as four or more modelling, e.g. five or more modelling, such as six or more modelling, e.g. seven or more modelling, selected from a microbial kinetic modelling; a production modelling; a growth rate modelling; a substrate modelling; a stoichiometric modelling; a mechanical modelling (mixing rate, the size of the U-loop fermenter, the flow rate, the pressure generating devices, the temperature regulating devices); or a U-loop fermenter design modelling.

In a preferred embodiment of the present invention, wherein the at least one mathematic analysis involves a modelling of one or more substrates or metabolites inhibiting the growth of the microorganism in the U-loop fermenter. Preferably, the one or more substrates or metabolites inhibiting the growth of the microorganism in the U-loop fermenter may be methane, methanol, nitrite, nitrate, ammonium, acid, or derivatives hereof.

When the substrate is methane, the substrate/methane may be provided in the form of biogas, natural gas, syngas or pure methane gas.

In another embodiment of the present invention the at least one mathematic analysis involves a modelling of one or more factors inhibiting or reducing the growth of the microorganism present in the U-loop fermenter. Preferably, the one or more factor(s) may include temperature, pressure, flowrate and/or pH.

The mathematical analysis may involve an evaluation of a test value relative to one or more control values in respect of the specific parameter. In an embodiment of the present invention the control value may be provided as at least one calculated control value.

In an embodiment of the present invention the processor may be configured to dynamically adjust and/or optimize the fermentation process based on the multiple database entries representing the test value and the multiple database entries representing the control value.

In a preferred embodiment of the present invention the computer may be provided with a feedback modelling.

In the present context, the term "feedback modulation" relates to A dynamical system that change behavior over time. The change behavior over time may be in a response to internal stimulation; external stimulation or forcing.

In feedback modulation based on internal stimulation the system may change dynamically in response to a difference between the test value (or the calculated test value) and the control value (or the calculated control value).

The term feedback modulation based on external stimulation refers to a situation in which two (or more) dynamical systems (U-loop fermenters) are connected together such that each system (U-loop fermenter) influences the other and their dynamics are thus strongly coupled. In such structure, the first system (U-loop fermenter) may influence the second system (U-loop fermenter) and the second system (U-loop fermenter) may influence the first system (U-loop fermenter), leading to a circular modulation.

In a preferred embodiment of the present invention, the processor may be configured to dynamically adjust and/or optimize the fermentation process, e.g. based on feedback modelling.

In order to provide test values and/or control values to the database the system comprises one or more analysis apparatus for detecting at least one parameter of the fermentation process.

In an embodiment of the present invention the parameter may be selected from the group consisting of biomass yield, biomass growth rate, pH, nitrate content, dissolved content of methane, gaseous content of methane, dissolved content of oxygen, gaseous content of oxygen; methanol content, nitrite content, nitrate content, ammonium content, salt content, temperature, pressure inside the U-loop fermenter, flow rate, speed of the agitator, the circulation pump, or the pressure over the gas sparger.

The parameters may be analysed in one or more analysis apparatus. Preferably, the one or more analysis apparatus comprises one or more sensors, such as on-line sensors, by-pass systems or the like.

The control value may be a control value of the at least one parameter and/or the control value may be a control value of at least one product control parameter.

The system may further comprise at least one product analysis apparatus for repetitively providing a product test value of at least one product test parameter of one U-loop fermenter.

The system may preferably further comprise a data interface for repetitively entering the product test value of the at least one product control parameter into the database.

The product control parameter may be selected from the group consisting of biomass yield, biomass growth rate, pH, nitrate content, dissolved content of methane, gaseous content of methane, dissolved content of oxygen, gaseous content of oxygen, or any combination hereof. The product control parameter may preferably be selected differently from the at least one parameter of the fermentation process.

In one embodiment of the present invention the control value may be based on a best modelled profile for the at least one parameter.

In another embodiment of the present invention the control value is based on the fermentation product obtained from the fermentation process, providing a product control value. Preferably, the fermentation product is different from the at least on parameter.

In a further embodiment of the present invention, the control value is based on both a best modelled profile for the at least one parameter and on the fermentation product obtained from the fermentation process, providing a product control value. Preferably, the fermentation product is different from the at least one parameter.

A further aspect of the present invention relates to a method for adjusting and/or optimizing a fermentation process performed in at least one U-loop fermenter, the system comprising:
  repetitively providing at least one test value of at least one parameter of one U-loop fermenter, to at least one analysis apparatus;
  repetitively entering the test value of the at least one parameter in a database of a computer comprising a processor;
  repetitively entering at least one control value in a database of a computer comprising a processor;
  wherein the database is adapted to store multiple database entries representing the test value of the at least one parameter at various points in time and adapted to store multiple database entries representing the control value at various points in time, wherein the processor is programmed to:
    perform at least one mathematical analysis of the test value providing a calculated test value, and/or the control value providing at least one calculated control value; and
    selecting, on the basis of the calculated test value and/or on the calculated control value, the adjustment to be introduced into at least one other U-loop fermenter, to benefit from the change made in the one U-loop fermenter.

In an embodiment of the present invention the control value is a control value of the at least one parameter and/or the control value is a control value of at least one product control parameter.

In accordance with the present invention the test values and/or the control values may preferably be provided at a dynamic sampling interval.

In an embodiment of the present invention the test values and/or the control values are provided at a sampling interval in the range of 1 minute to 10 hours, such as in the range of 2 minutes and 5 hours, e.g. in the range of 3 minutes and 1 hour, such as in the range of 4 minutes and 30 minutes, e.g. in the range of 5 minutes and 10 minutes.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Example 1

The present example shows a modelling of a fermentation process of the methanotrophs, *Methylococcus capsulatus*.

Methanotrophs can grow on cheap carbon sources such as methane or methanol. They have a high protein content and can be used to produce single-cell protein (SCP). SCP can be used for animal feed and thereby sustain an increasing human population. In the preset example, the SCP is produced by using a U-loop fermenter. However, the operation of such a reactor and in particular the start-up phase of such fermentation is non-trivial and there is increased risk of failure and/or a reduced process productivity. In the present example, the present inventors a mathematical model that describes the dynamics of SCP production in a U-loop fermemter and an economic optimizing control was used to compute the optimal start-up profile for SCP production in a U-loop fermenter. Computation and implementation of the optimal start-up profile may be challenging as the optimal profile turns out to be an unstable attractor.

The Mathematical Model of Single-Cell Protein Production in a U-Loop Fermenter

Figure 1B:
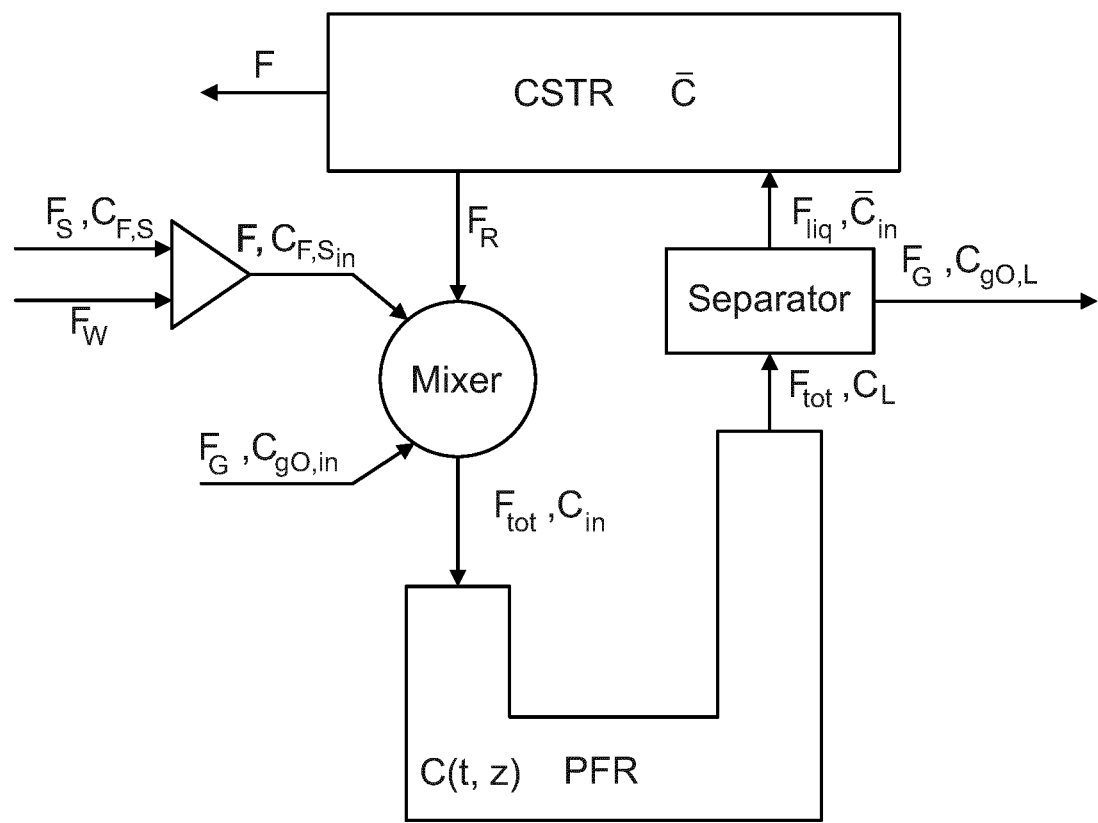
FIG. 1B shows an illustration of the conceptual elements making up the U-loop reactor and used in a mathematical model describing single cell protein (SCP) production in the U-loop reactor.

FIG. 1A shows a diagram of the U-loop fermenter and FIG. 1B shows an illustration of the conceptual elements making up the U-loop fermenter and used in a mathematical model describing single cell protein (SCP) production in the U-loop fermenter.

The substrate used in the present example (methanol), together with water, and gas (oxygen) is fed to the reactor at the media inlet at the upper part of the U-loop leg. These feed streams are mixed with the recycle stream from the top tank that is modelled as a continuous stirred tank reactor (CSTR) with constant liquid volume. This two-phase liquid-gas mixture flows through the U-loop-part of the fermenter which is modelled as a PFR. The separation of gas and liquid when the fast flowing stream enters the top tank from the U-loop leg is modelled as a static ideal gas-liquid separator.

Stoichiometry, Kinetics and Production Rate

The growth of *M. capsulatus* can be approximated by the overall reaction (1):

$$Y_{XS}CH_3OH + Y_{XN}HNO_3 + Y_{XO}O_2 ? X + Y_{XC}CO_2 + Y_{XW}H_2O \quad (1)$$

using the stoichiometric coefficients provided in Table 1.

TABLE 1

| | | Yield coefficients | | | |
|---|---|---|---|---|---|
| | i | $Y_{si}$ [mol/mol] | $Y_{xi}$ [mol/mol] | $M_{wi}$ [g/mol] | $W_{xi}$ [g/g] |
| $CH_3OH$ | S | 1.000 | 1.366 | 32.042 | 1.778 |
| $HNO_3$ | N | 0.146 | 0.199 | 63.013 | 0.510 |
| $O_2$ | O | 0.439 | 0.600 | 31.999 | 0.779 |
| $CH_{1.8}O_{0.5}N_{0.2}$ | X | 0.732 | 1.000 | 24.626 | 1.000 |
| $CO_2$ | C | 0.268 | 0.366 | 44.010 | 0.654 |
| $H_2O$ | W | 1.415 | 1.933 | 18.015 | 1.414 |

The specific growth rate, p, of *M. capsulatus* is limited by the substrate and the dissolved oxygen:

$$\mu = \mu(C_S, C_O) = \mu_{max}\mu_S(C_S)\mu_O(C_O), \quad (2a)$$

where the specific growth rate factors are governed by:

$$\mu_S(C_S) = \frac{C_S}{K + C_S + C_S^2/K_I}, \quad (2b)$$

$$\mu_O(C_O) = \frac{C_O}{K_O + C_O}. \quad (2c)$$

The production rates of biomass (X), substrate (S), and dissolved oxygen (O) are:

$$R_X = R_X(C_X, C_S, C_O) = \mu(C_S, C_O)C_X, \quad (3a)$$

$$R_S = R_S(C_X, C_S, C_O) = -\gamma_S R_X, \gamma_S = \frac{M_{wS}}{M_{wX}Y_{SX}}, \quad (3b)$$

$$R_O = R_O(C_X, C_S, C_O) = -\gamma_O R_X, \gamma_O = \frac{M_{wO}Y_{SO}}{M_{wX}Y_{SX}}. \quad (3c)$$

Mixing Section

The liquid flow rate in the PFR section is:

$$F_L = F_R + F_S + F_W. \quad (4)$$

The gas inlet flow rate, $F_G$, is also the flow rate of the gas phase in the PFR section. The inlet concentrations in the liquid phase (X, S, O) and the gas phase (gO) to the PFR section as shown in FIG. 1B are:

$$C_{X,in} = \frac{F_R \overline{C}_X}{F_L}, \ C_{S,in} = \frac{F_S C_{F,S} + F_R \overline{C}_S}{F_L}, \ C_{O,in} = \frac{F_R \overline{C}_O}{F_L}, \quad (5)$$

$$C_{gO,in} = C_{F,O},$$

where $\overline{C}_X$, $\overline{C}_S$, and $\overline{C}_O$ denote the concentration in the CSTR section (top tank).

U-Loop Modelled as a PFR

The inlet boundary conditions to the PFR section are the flux specification by the velocity and the inlet concentrations as:

$$N_i(t,0) = v C_{i,in}(t), i \in \{X, S, O, gO\}. \quad (6)$$

The velocity is computed as $v = (F_L + F_G)/A$. A is the cross-sectional area of the U-loop pipe. Mass conservation in the U-loop pipe is described by the following system of partial differential equations:

$$\frac{\partial C_X}{\partial t} = -\frac{\partial N_X}{\partial z} + R_X, \quad (7a)$$

$$\frac{\partial C_S}{\partial t} = -\frac{\partial N_S}{\partial z} + R_S, \quad (7b)$$

$$\frac{\partial C_O}{\partial t} = -\frac{\partial N_O}{\partial z} + R_O + \frac{1}{1-\varepsilon} J_{gl,O}, \quad (7c)$$

$$\frac{\partial C_{gO}}{\partial t} = -\frac{\partial N_{gO}}{\partial z} - \frac{1}{\varepsilon} J_{gl,O}, \quad (7d)$$

for $t_a \leq t \leq t_b$ and $0 \leq z \leq L$. Note that the concentrations. $C_i = C_i(t,z)$, and the fluxes, $N_i = N_i(C_i(t,z))$ for $i \in \{X, S, O, gO\}$ area function of time, t, and position, z, in the U-loop pipe. The production rates, ($R_X$, $R_S$, $R_O$), are also a function of time and position through their dependency on $C_X$, $C_S$, and $C_O$. The gas fraction is $$\varepsilon = \frac{F_G}{F_L + F_G}.$$

the gas-liquid transport of oxygen. The outlet of the PFR is governed by the Danekwerts boundary conditions $$\frac{\partial C_i}{\partial z}(t, L) = 0, \ i \in \{X, S, O, gO\}. \quad (8)$$

The flux in the PFR consist of convection and diffusion described by Fick's law:

$$N_i = v C_i + J_i, \ J_i = -D_i \frac{\partial C_i}{\partial z}, \ i \in \{X, S, O, gO\}. \quad (9)$$

The gas-liquid transport rate of oxygen is governed by:

$$J_{gl,O} = (k_L a)_O (C_{O,sat} - C_O), \ C_{O,sat} = \frac{P_O}{H_O} = \frac{RT}{M_{wO} H_O} C_{gO}, \quad (10)$$

where Henry's law in combination with the ideal gas law provides the oxygen saturation concentration.

Gas-Liquid Separating Section

When the fast flow liquid mixture enters the top tank from the U-loop pipe, it is assumed that gas and liquid are perfectly and instantaneously separated. This is modelled as an ideal static gas-liquid separator, where the gas phase is completely removed and the liquid phase enters the liquid phase of the top tank.

Top Tank Modelled as a CSTR

The top tank is modelled as a CSTR with a constant liquid volume. The mass balances are:

$$\frac{d\overline{C}_i}{d_t} = \overline{D} \overline{C}_{i,in} - \overline{D} \overline{C}_i + R_i(\overline{C}_X, \overline{C}_S, \overline{C}_O), \ i = \{X, S, O\}. \quad (11)$$

$\overline{D} = \overline{F}/\overline{V}$, is the dilution rate, for the constant liquid volume, $\overline{V}$, and the total in- and outflow rate, $\overline{F} = F_L$. When the top tank is operated with a constant liquid volume, the product flow rate is $F = \overline{F} - F_R = F_S + F_W$. The inlet concentrations to the liquid phase of the top tank are the liquid phase concentrations at the outlet of the PFR $$\overline{C}_{i,in}(t) = C_i(t, L), i \in \{X, S, O\}. \quad (12)$$

Economic Optimizing Optimal Control of the Start-Up

The profit of operation is the value of the produced biomass (SCP) minus the cost of raw materials. The cost of raw materials is approximated by the cost of substrate and the cost of oxygen. This can be expressed as ($p_X$ is the unit value of biomass (SCP), $p_S$ the unit cost of substrate, $p_O$ the unit cost of oxygen):

$$\phi \int_{t_a}^{t_b} p_X(R_X(\overline{C}_X(t), \overline{C}_S(t), \overline{C}_O(t)) \\ \overline{V} + \int_0^L R_X(C_X(t,z), C_S(t,z), C_O(t,z)) A dz) dt - \int_{t_a}^{t_b} (p_S F_S(t) + p_O F_G) dt \ (13)$$

which is identical to $$\phi = \int_{t_a}^{t_b} (pxF(t)\overline{C}_X(t) - p_S F_S(t) - p_O F_{gO}(t)) dt + px(\overline{C}_X(t_b) \\ \overline{V} + \int_0^L C_X(t_b, z) A dz) - px(\overline{C}_X(t_a) \overline{V} + \int_0^L C_X(t_a, z) A dz). \quad (14)$$

The structure of the model is such that this profit function increases for increasing biomass concentrations, $C_X$, as $R_X = \mu(C_S, C_O) C_X$. A number of phenomena, e.g. such as reduced gas-liquid mass transport at high viscosity due to high biomass concentration, are not included in the model. To avoid unrealistically high biomass concentrations, an upper limit, $C_{X,max}$, is enforced through the output constraints:

| $0 \leq \overline{C}_X(t) \leq C_{X,max}$, | $t_a \leq t \leq t_b$, | (15a) |
|---|---|---|
| $0 \leq C_X(t, z) \leq C_{X,max}$, | $t_a \leq t \leq t_b, 0 \leq z \leq L$, | (15b) | and it is assumed that this maximum is well below limits where e.g. the gas-liquid mass transport starts to change due to viscosity effects. We have similar bounds on the other concentration variables, but they are never active. In addition, the manipulated variables, ($F_W$, $F_S$, $F_G$), are bounded by the input constraint:

$$0 \leq F_W(t) \leq F_{W,\,max}, \quad t_a \leq t \leq t_b, \quad (16a)$$
$$0 \leq F_S(t) \leq F_{S,\,max}, \quad t_a \leq t \leq t_b, \quad (16b)$$
$$0 \leq F_G(t) \leq F_{G,\,max}, \quad t_a \leq t \leq t_b, \quad (16c)$$

The optimal control defining the optimal start-up and operation of the U-loop reactor consists of computing, the profiles of e manipulated variables, $[F_W(t), F_S(t), F_G(t)]_{t_a}^{t_b}$, such that 1) the economic objective function, $\phi$, is maximized, 2) the model presented in Section 2 is respected, and 3) the constraints (15) and (16) are satisfied. We discretize the input profile using a zero-order-hold (piecewise constant) discretization. It turns out that the optimal start-up profile is unstable, and the single-shooing method does not converge. The multiple-shooting method as well as the simultaneous method converge toward the optimal unstable start-up profile. Consequently, we use the simultaneous method for computing the optimal operating profiles, $[F_W^*(t), F_S^*(t), F_G^*(t)]_{t_a}^{t_b}$, from the initial time, $t_a$, to the final time, $t_b$.

Figure 2:
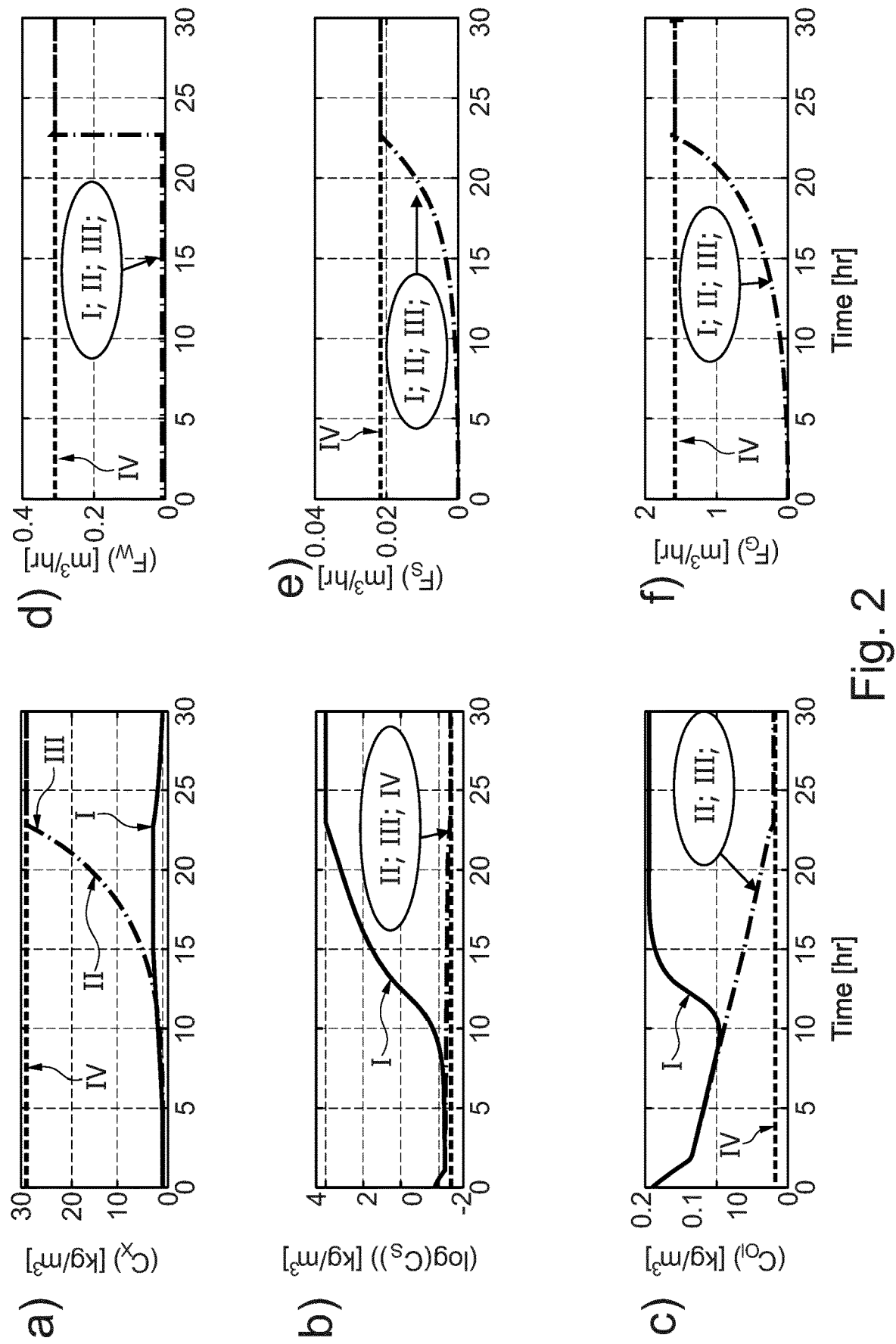
FIG. 2 shows the optimal start-up profiles (the batch profiled or the fed-batch profiles) and the corresponding concentrations.
Figure 3:
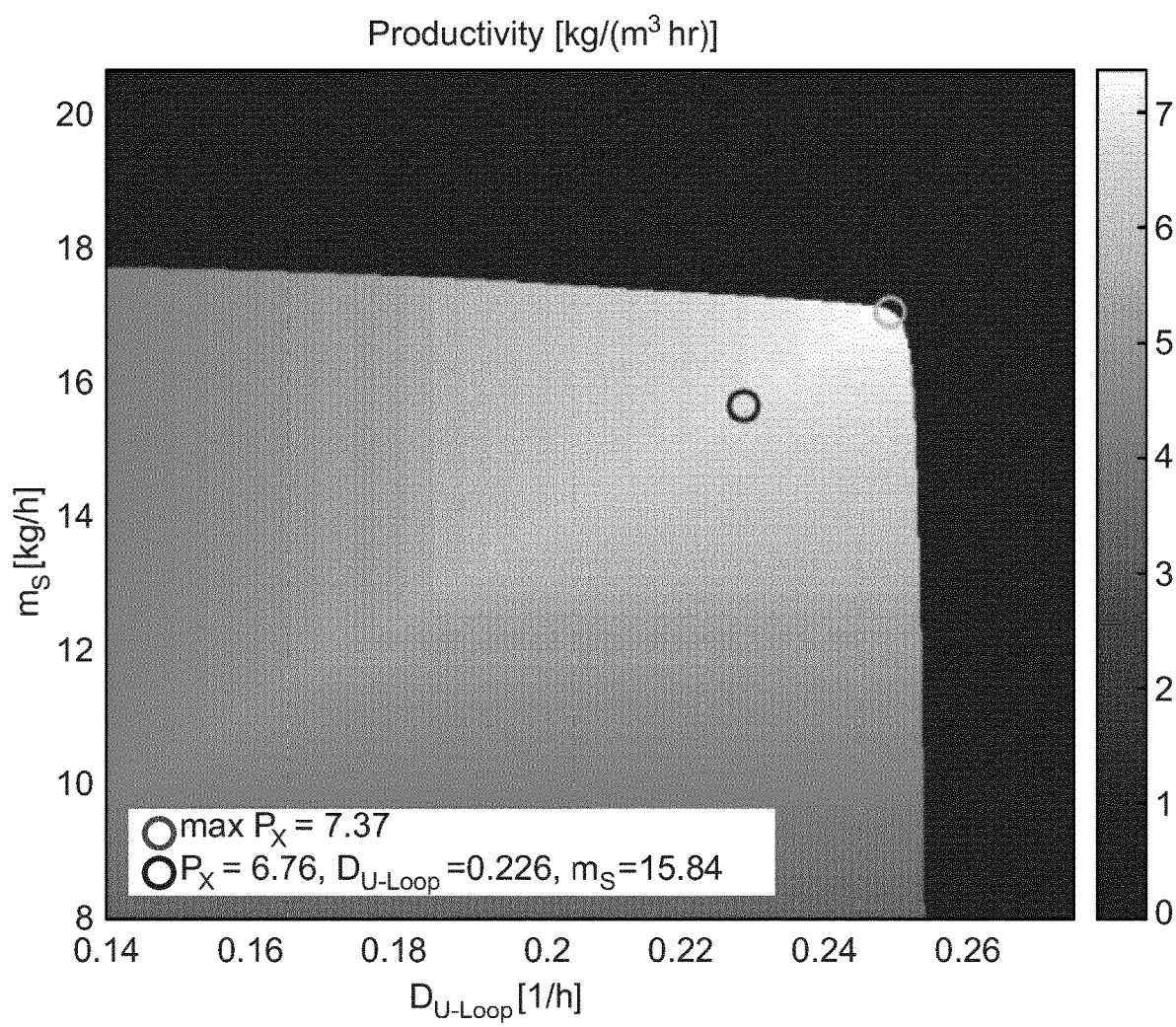
FIG. 3 shows U-Loop reactor biomass productivity computed by the optimal start-up profile at steady state. The black region corresponds to zero productivity. The black circle indicates the operating point for the given value, such as the substrate methanol, of manipulated variables using the traditional fermentation processes and the white/gray circle indicates the operating point for the given value, e.g. the substrate methanol, of manipulated variables using the system and the method according to the present invention. The abbreviation $m_S$ relates to the substrate mass rate, such as the mass rate of methanol, during the start-up phase. The abbreviation $D_{U\text{-}Loop}$ relates to the dilution rate of the U-Loop reactor during the start-up phase. The on the right-hand side going from 1 to 7 indicates the productivity of the start-up phase in kg/m$^2$/hour.

FIG. 2 shows the optimal start-up profiles, $[F_W^*(t), F_S^*(t), F_G^*(t)]_{t_a}^{t_b}$, and the corresponding concentration, $[\overline{C}_W^*(t), \overline{C}_S^*(t), \overline{C}_O^*(t)]_{t_a}^{t_b}$, in the top tank, when the optimal-startup is computed, using the simultaneous method (blue). The black-curves show the simulated states in the top tank when the optimal profile, $[F_W^*(t), F_S^*(t), F_G^*(t)]_{t_a}^{t_b}$, is implemented in open-loop. Clearly, the optimal state profiles and the state-profiles obtained by an open-loop implementation diverges around t=8 hr for the substrate concentration and t=13 hr for the biomass concentration. This is another indication that the optimal start-up profile in an unstable attractor. Accordingly, it is not possible to achieve high and profitable biomass concentration by an open-loop implementation of the optimal start-up profiles. If the optimal start-up profile is implemented using a P-controller with clipping for the substrate flow rate $$\tilde{F}_S = F_S^* K_{cS}(\overline{C}_S - \overline{C}_S^*), \quad (17a)$$

$$F_S = \max\{0, \min\{\tilde{F}_S, F_{S,max}\}\}, \quad (17b)$$

the achieved start-up profile (red curves that are hardly distinguishable from the blue curves) are very similar to the optimal start-up profile (blue curves). This demonstrates nicely that the optimal start-up of the U-loop fermenter for production of single-cell protein requires feedback. The green curves show the optimal steady-state operating point.

CONCLUSIONS

We presented a model describing the dynamics of SCP production by methanotrophs in a U-loop fermenter. We also presented economic objective functions and constraints that can be used to formulate an economic optimizing optimal control problem for SCP production in the U-loop fermenter. The model can be used for economic optimizing control of the U-loop fermenter in continuous operation as well as during start-up. Interestingly from a numerical perspective, the optimal start-up profile is unstable and either multiple-shooting or the simultaneous method must be used for dynamic optimization. Due to the instability, the single-shooting method does not work well. By simulation we demonstrate that economic optimizing control provides an optimal start-up profile that is unstable.

Therefore, it cannot be implemented in an open-loop fashion but must be stabilised by e.g. a P-controller for the substrate concentration.

The invention claimed is:

1. A system for adjusting and/or optimize a fermentation process performed in at least one U-loop fermenter, the system comprising:
   at least one U-loop fermenter being operatively connected to a computer
   the computer comprising a processor and being operatively connected to a database;
   at least one analysis apparatus for repetitively providing a test value of at least one parameter of one U-loop fermenter;
   a data interface for repetitively entering the test value of the at least one parameter in the database,
   the database comprising at least one control value,
   wherein the database is adapted to store multiple database entries representing the test value of the at least one parameter at various points in time and adapted to store multiple database entries representing the at least one control value at various points in time, wherein the processor is programmed to:
   perform at least one mathematical analysis of the test value providing a calculated test value, and/or the at least one control value providing at least one calculated control value;
   selecting, on the basis of the calculated test value and/or on the at least one calculated control value, an adjustment to be introduced into at least one other U-loop fermenter to benefit from a change made in the at least one U-loop fermenter;
   wherein the at least one mathematic analysis comprises that one or more substrates or metabolites are modelled, wherein the one or more substrates or metabolite inhibit growth of a microorganism in the at least one U-loop fermenter, and wherein the one or more substrates or metabolites, which are modelled in the mathematical analysis is or are selected from the group consisting of nitrite, nitrate, ammonium, an acid or a derivative hereof; and
   wherein the at least one mathematical analysis comprises a modelling of a conceptually partitioned U-loop fermenter into sections or parts.

2. The system according to claim 1, wherein the at least one mathematical analysis involves a state estimator and, wherein the state estimator involves a Kalman Filter, an Extended Kalman Filter, an Unscented Kalman Filter, an Ensemble Kalman Filter, a Particle Filter, or a Moving Horizon Estimator, or a variation of one or more of these filters.

3. The system according to claim 1, wherein the at least one mathematical analysis involves a model regulator and wherein the model regulator involves a model predictive control, a linear model regulator, a non-linear model regulator and/or
   wherein the model regulator is based on knowledge on physical processes, on chemical and biochemical processes, data-driven models, a combination of data-driven and first-principles models, and/or wherein the model regulator is based on a linear MPC, an economic linear MPC, a non-linear MPC, an economic non-linear MPC.

4. The system according to claim 1, wherein the at least one mathematical analysis involves a model controller and/or wherein the model controller involves a proportional (P) controller, a proportional-integral (PI) controller and/or a proportional-integral-derivative (PID) controller.

5. The system according to claim 1, wherein the one or more substrates or metabolites inhibiting the growth of the microorganism in the at least one U-loop fermenter may be methanol, or a derivative hereof.

6. The system according to claim 1, wherein the at least one mathematic analysis involves a modelling of one or more factors inhibiting or reducing the growth of the microorganism in the at least one U-loop fermenter.

7. The system according to claim 1, wherein the system is provided for a start-up phase (a batch phase) of the fermentation process.

8. The system according to claim 1, wherein the fermentation process is a bacterial fermentation process.

9. The system according to claim 8, wherein the bacteria cultivated in the bacterial fermentation process comprises a methanotrophic bacteria.

10. The system according to claim 9, wherein the methanotrophic bacteria is *Methylococcus capsulatus*.

11. A method for adjusting and/or optimize a fermentation process performed in at least one U-loop fermenter, the method comprising:
- repetitively providing at least one test value of at least one parameter of one U-loop fermenter to at least one analysis apparatus;
- repetitively entering the test value of the at least one parameter in a database of a computer comprising a processor;
- repetitively entering at least one control value in a database of a computer comprising a processor;

wherein the database is adapted to store multiple database entries representing the test value of the at least one parameter at various points in time and adapted to store multiple database entries representing the at least one control value at various points in time, wherein the processor is programmed to:
- perform at least one mathematical analysis of the test value providing a calculated test value, and/or the at least one control value providing at least one calculated control value;
- selecting, on the basis of the calculated test value and/or on the calculated at least one control value, an adjustment to be introduced into at least one other U-loop fermenter to benefit from a change made in the at least one U-loop fermenter;

wherein the at least one mathematic analysis comprises that one or more substrates or metabolites are modelled, wherein the one or more substrates or metabolites inhibit growth of a microorganism in the at least one U-loop fermenter, and wherein the one or more substrates or metabolites, which are modelled in the mathematical analysis is or are selected from a group consisting of nitrite, nitrate, ammonium, an acid or a derivative hereof; and wherein the at least one mathematical analysis comprises a modelling of a conceptually partitioned U-loop fermenter into sections or parts.

* * * * *